United States Patent
Tuysuzoglu et al.

(10) Patent No.: US 11,664,125 B2
(45) Date of Patent: May 30, 2023

(54) SYSTEM AND METHOD FOR DEEP LEARNING BASED CARDIAC ELECTROPHYSIOLOGY MODEL PERSONALIZATION

(71) Applicant: Siemens Healthcare GmbH, Erlangen (DE)

(72) Inventors: Ahmet Tuysuzoglu, Plainsboro, NJ (US); Tiziano Passerini, Plainsboro, NJ (US); Shun Miao, Princeton, NJ (US); Tommaso Mansi, Plainsboro, NJ (US)

(73) Assignee: Siemens Healthcare GmbH, Erlangen (DE)

(*) Notice: Subject to any disclaimer, the term of this patent is extended or adjusted under 35 U.S.C. 154(b) by 1355 days.

(21) Appl. No.: 15/593,890

(22) Filed: May 12, 2017

(65) Prior Publication Data
US 2017/0330075 A1   Nov. 16, 2017

Related U.S. Application Data

(60) Provisional application No. 62/335,440, filed on May 12, 2016.

(51) Int. Cl.
*G16H 50/20* (2018.01)
*G06N 3/08* (2023.01)
(Continued)

(52) U.S. Cl.
CPC ........... *G16H 50/20* (2018.01); *A61B 5/7264* (2013.01); *G06F 30/23* (2020.01); *G06N 3/045* (2023.01);
(Continued)

(58) Field of Classification Search
CPC ........ G16H 50/20; G16H 50/50; G06F 30/23; G06F 19/00; A61B 5/7264; G06N 3/0454;
(Continued)

(56) References Cited

U.S. PATENT DOCUMENTS 6,601,049 B1 * 7/2003 Cooper ............... G06N 3/0454
706/2
7,916,919 B2 3/2011 Zheng et al.
(Continued)

OTHER PUBLICATIONS

Zettinig, O., et al., Data-driven estimation of cardiac electrical diffusivity from 12-lead ECG signals, Medical Image Analysis. vol. 18, 2014. p. 1361-1376 (Year: 2014).*
(Continued)

*Primary Examiner* — Keith M Raymond
*Assistant Examiner* — Sean A Frith (57) ABSTRACT

A method and system for deep learning based cardiac electrophysiological model personalization is disclosed. Electrophysiological measurements of a patient, such as an ECG trace, are received. A computational cardiac electrophysiology model is personalized by calculating patient-specific values for a parameter of the computational cardiac electrophysiology model based at least on the electrophysiological measurements of the patient using a trained deep neural network (DNN). The parameter of the computational cardiac electrophysiology model corresponds to a spatially varying electrical cardiac tissue property.

25 Claims, 7 Drawing Sheets

(51) Int. Cl.
*G16H 50/50* (2018.01)
*G06N 7/08* (2006.01)
*G06N 3/082* (2023.01)
*G06F 30/23* (2020.01)
*A61B 5/00* (2006.01)
*G16Z 99/00* (2019.01)
*G06N 3/045* (2023.01)
*G06N 20/00* (2019.01)
*G06N 3/048* (2023.01)
*G06N 5/01* (2023.01)
*G06N 7/01* (2023.01)

(52) U.S. Cl.
CPC ............ *G06N 3/08* (2013.01); *G06N 3/082* (2013.01); *G06N 7/08* (2013.01); *G16H 50/50* (2018.01); *G16Z 99/00* (2019.02); *G06N 3/048* (2023.01); *G06N 5/01* (2023.01); *G06N 7/01* (2023.01); *G06N 20/00* (2019.01)

(58) Field of Classification Search
CPC ........... G06N 3/08; G06N 3/082; G06N 7/08; G06N 20/00; G06N 3/0481; G06N 5/003; G06N 7/005
See application file for complete search history.

(56) References Cited

U.S. PATENT DOCUMENTS

| | | | |
|---|---|---|---|
| 9,129,053 | B2 | 9/2015 | Mansi et al. |
| 9,277,970 | B2 | 3/2016 | Mansi et al. |
| 9,463,072 | B2 | 10/2016 | Comaniciu et al. |
| 2007/0258649 | A1* | 11/2007 | Bach ................ G06V 10/454 382/226 |
| 2007/0270703 | A1* | 11/2007 | He ................ G06K 9/0057 600/509 |
| 2010/0040272 | A1 | 2/2010 | Zheng et al. |
| 2012/0022843 | A1 | 1/2012 | Onasec et al. |
| 2013/0197881 | A1 | 8/2013 | Mansi et al. |
| 2013/0226542 | A1 | 8/2013 | Rapaka et al. |
| 2014/0022250 | A1* | 1/2014 | Mansi ................ A61B 34/10 345/420 |
| 2014/0136174 | A1 | 5/2014 | Audigier et al. |
| 2015/0042464 | A1 | 2/2015 | Yu et al. |
| 2015/0112182 | A1* | 4/2015 | Sharma ............ A61B 5/7264 600/408 |
| 2015/0294082 | A1 | 10/2015 | Passerini et al. |
| 2015/0347709 | A1 | 12/2015 | Mansi et al. |
| 2016/0058520 | A1 | 3/2016 | Yang et al. |
| 2016/0148078 | A1* | 5/2016 | Shen ................ G06K 9/66 382/158 |
| 2016/0210435 | A1 | 7/2016 | Neumann et al. |
| 2016/0210550 | A1* | 7/2016 | Merrill ............ G06N 3/0454 |
| 2016/0220311 | A1 | 8/2016 | Mansi et al. |
| 2016/0283687 | A1 | 9/2016 | Kamen et al. |
| 2016/0306943 | A1* | 10/2016 | Choi ................ A61B 5/72 |
| 2017/0027649 | A1 | 2/2017 | Kiraly et al. |
| 2017/0068796 | A1 | 3/2017 | Passerini et al. |
| 2017/0185740 | A1 | 6/2017 | Seegerer et al. |

OTHER PUBLICATIONS

Harmouche, R., et al., "Patient-specific model of a scoliotic torso for surgical planning," Medical Imaging 2013: Image-Guided Procedures, Robotic Interventions, and Modelling. SPIE Medical Imaging, 2013. p. 1-7 (Year: 2013).*

Ashikaga, H., et al., "Feasibility of Image-Based Simulation to Estimate Ablation Target in Human Ventricular Arrhythmia," Heart Rhythm. vol. 10(8), 2013. p. 1109-1116 (Year: 2013).*

Chinchapatnam, P., et al., "Model-Based Imaging of Cardiac Apparent Conductivity and Local Conduction Velocity for Diagnosis and Planning of Therapy," IEEE Transactions on Medical Imaging. vol. 27(11), 2008. p. 1631-1642 (Year: 2008).*

Hurtado, D., et al., "Computational modeling of electrocardiograms: Repolarization and T-wave polarity in the human heart," Computational Methods Biomechanical Biomedical Engineering. vol. 17(9), 2014. p. 986-996 (Year: 2014).*

Prakosa, A., et al., "Cardiac Electrophysiological Activation Pattern Estimation From Images Using a Patient-Specific Database of Synthetic Image Sequences," IEEE Transactions on Biomedical Engineering. vol. 61(2), 2014. p. 235-245 (Year: 2014).*

Kiranyaz, S., et al., "Real-Time Patient-Specific ECG Classification by 1-D Convolutional Neural Networks," IEEE Transactions on Biomedical Engineering. vol. 63(3), 2016. p. 664-675 (Year: 2016).*

Sansone, M., et al., "Electrocardiogram Pattern Recognition and Analysis Based on Artificial Neural Networks and Support Vector Machines: A Review," Journal of Healthcare Engineering. vol. 4(4), 2013. p. 465-504 (Year: 2013).*

Zhang, J., "Clinical Application of Electrocardiographic Imaging in Patients with Ischemic Cardiomyopathy, Early Repolarization Syndrome and Brugada Syndrome," Washington University Open Scholarship. 2015. p. 1-132 (Year: 2015).*

Jiang, M., Lv, J., Wang, C., Huang, W., Xia, L., & Shou, G. (Sep. 2011). A hybrid model of maximum margin clustering method and support vector regression for solving the inverse ECG problem. In Computing in Cardiology, 2011 (pp. 457-460). IEEE.

Auricchio, Angelo, and Frits W. Prinzen. "Non-responders to cardiac resynchronization therapy." Circulation Journal 75.3 (2011): 521-527.

Zettinig, Oliver, et al. "Data-driven estimation of cardiac electrical diffusivity from 12-lead ECG signals." Medical image analysis 18.8 (2014): pp. 1361-1376. Medical Image Analysis, vol. 18, No. 8.

Prakosa Adityo et al: "Cardiac Electrophysiological Activation Pattern Estimation From Images Using a Patient-Specific Database of Synthetic Image Sequences", IEEE Transactions on Biomedical Engineering, IEEE Service Center, Piscataway, NJ, USA, vol. 61, No. 2, Feb. 1, 2014, pp. 235-245.

* cited by examiner

SYSTEM AND METHOD FOR DEEP LEARNING BASED CARDIAC ELECTROPHYSIOLOGY MODEL PERSONALIZATION

This application claims the benefit of U.S. Provisional Application No. 62/335,440, filed May 12, 2016, the disclosure of which is herein incorporated by reference in its entirety.

BACKGROUND OF THE INVENTION

The present invention relates to automatic personalization of an electrophysiology model, and more particularly to automatic deep learning based personalization of an electrophysiology model from medical images and electrophysiology measurements of a patient.

Physiological measurements, such as electrocardiography (ECG), have been widely used as a diagnostic tool by cardiologists to detect potential rhythmic and structural problems. In particular, rule-based strategies are used to relate abnormalities in the physiological signals to possible diagnosis and treatment decisions. A list of such rule-based strategies can be found in common medical textbooks. Although such rules are typically used for direct diagnosis and treatment of patients from physiological measurements, it has been reported that approximately 30% of patients do not respond to invasive cardiac interventions, such as radiofrequency ablation and cardiac resynchronization therapy (CRT), even though they are within the guidelines for such treatments under the rule-based strategies.

Computer-based cardiac model personalization has been proposed as a diagnostic and predictive tool for patient-specific evaluation of physiological and image based measurements. As a diagnostic tool, personalization of a cardiac electrophysiological model can provide a detailed layout of cardiac tissue characteristics, such as conduction velocities or transmembrane potentials, which can provide a more accurate diagnosis of cardiac problems than a diagnosis directly from physiological measurements (e.g., ECG) using the traditional rule-based strategies. As a predictive tool, once a cardiac electrophysiological model is personalized, outcomes of various clinical cardiac interventions, such as radio-frequency ablation and CRT, can be simulated for the patient using the personalized cardiac electrophysiological model to assess the effectiveness and to determine optimal treatment parameters.

Cardiac model personalization typically relies on a forward computational model that relates cardiac action potentials to body surface potentials that are acquired using ECG or other sensory devices. Many types of forward models exist, mainly differing on the level of abstraction (i.e., cellular level) they assume. Typically, there is a tradeoff between the complexity and the computational load of the forward model. Parameters of the cardiac model are personalized by solving an inverse problem, which is defined as the estimation of cardiac model parameters given the body surface potentials. The conventional way of solving the inverse problem is by optimizing a fidelity function of observations and the forward model computations. Since the forward model is not tractable for differentiation, derivative-free optimizers are used for optimization of the fidelity function. A downside to using derivative-free optimizers is that a large number of forward model calls is typically required, which scales the number of parameters to be estimated leading to a high computational cost and preventing real time operation. Furthermore, such optimizers are prone to getting stuck at local optima and the optimization outcomes are initialization dependent.

BRIEF SUMMARY OF THE INVENTION

The present invention provides a method and system for deep learning based cardiac electrophysiological model personalization. Embodiments of the present invention utilize a trained deep neural network (DNN) to estimate spatially varying personalized parameters of a cardiac electrophysiological model based on medical images and electrophysiological measurements of a patient. The personalized cardiac electrophysiological model can be used as a diagnostic tool for diagnosing cardiac conditions of the patient or a predictive tool to simulate various cardiac interventions and/or intervention parameters for the patient.

In one embodiment of the present invention, electrophysiological measurements of a patient are received. A computational cardiac electrophysiology model is personalized by calculating patient-specific values for a parameter of the computational cardiac electrophysiology model based at least on the electrophysiological measurements of the patient using a trained deep neural network (DNN). The parameter of the computational cardiac electrophysiology model corresponds to a spatially varying electrical cardiac tissue property.

These and other advantages of the invention will be apparent to those of ordinary skill in the art by reference to the following detailed description and the accompanying drawings.

DETAILED DESCRIPTION

The present invention relates to computer based personalization of a cardiac electrophysiological model. Embodiments of the present invention provide a method and system for deep learning based cardiac electrophysiological model personalization from medical images and electrophysiological measurements of a patient. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system or a remote computer system.

Cardiac electrophysiological (EP) model personalization refers to estimating/calculating personalized parameters of a cardiac EP model, such as conduction velocities and/or action potential durations, for a particular patient. Embodiments of the present invention use a deep learning architecture to personalize a cardiac EP model from medical images and EP measurements (e.g., ECG) of a patient. As the cardiac EP model parameters are spatially varying properties of the cardiac tissue, the personalization of the cardiac EP model results in a patient-specific mapping of such spatially varying tissue properties over the patient's heart. This patient-specific mapping of cardiac EP tissue properties provides valuable diagnostic information that would otherwise be unavailable without an invasive cardiac EP mapping procedure. In addition, once personalized, the cardiac EP model can be used to simulate cardiac EP of the patient, resulting in computation of patient-specific time varying transmembrane potentials at different locations of the patient's heart. The patient-specific simulated transmembrane potentials provide additional valuable diagnostic information for diagnosing cardiac conditions and selecting treatments for a patient. The personalized cardiac EP model can also be used to simulate various cardiac interventions, such as radio-frequency ablation and cardiac resynchronization therapy (CRT), using different intervention parameters/protocols to assess the effectiveness of the cardiac interventions for the patient.

Existing computer-based cardiac model personalization techniques typically solve the inverse problem of estimating cardiac EP model parameters given a set of observed body surface potentials by optimizing a fidelity function of observed body surface potentials and simulated body surface potentials computed using the computational cardiac EP model (i.e., the forward model). Since the forward model is not tractable for differentiation, derivative-free optimizers are used for optimization of the fidelity function. One downside to using derivative-free optimizers is that a large number of forward model calls is typically required, which scales the number of parameters to be estimated leading to a high computational cost and preventing real time operation. Furthermore, such optimizers are prone to getting struck at local optima and the optimization outcomes are initialization dependent.

Recently, data-driven approaches for computer-based cardiac EP model personalization have been proposed to circumvent the shortcomings of the inverse optimization approaches. For example, in A. Prokosa et al., "Cardiac Electrophysiological Activation Pattern Estimation from Images Using a Patient-Specific Database of Synthetic Image Sequences," *IEEE Transactions on Biomedical Engineering*, Vol. 61, No. 2, pp. 235-245, February 2014, a support vector regression framework is used for predicting depolarization times from regional kinematic descriptors in an approach that requires the training of a different model for each patient. In O. Zettinig et al., Data-Driven Estimation of Cardiac Electrical Diffusivity from 12-Lead ECG Signals," *Medical Image Analysis*, Vol. 18, No. 8, pp. 1361-1376, 2014, QRS and EA are used as features in a polynomial regression framework to predict conduction velocities of the left and right ventricles and the myocardium. In M. Jian et al., "A Hybrid Model of Maximum Margin-Clustering Method and Support Vector Regression for Solving the Inverse ECG Problem," in 2011 *Computing in Cardiology*, September 2011, pp. 457-460, a learning based approach was proposed that maps body surface potentials to transmembrane potentials by first clustering and then learning a different support vector regressor for each cluster.

Embodiments of the present invention use a trained deep learning architecture to estimate spatially varying parameters (e.g., conduction velocities) of a cardiac EP model from medical images and physiological measurements of a patient. Embodiments of the present invention provide various improvements over existing computer-based methods for cardiac EP model personalization. Instead of using features derived from ECG signals, such as QRS and EA, embodiments of the present invention uses the complete ECG signal traces as input to the deep learning architecture, which allows the deep learning architecture to learn discriminatory features from the data itself. This increases the robustness and accuracy of the EP model personalization as compared to the existing techniques. The trained deep learning architecture does not require training a new network for each patient and naturally incorporates patient-specific features, such as cardiac and torso geometry, during training. Unlike the inverse optimization based approaches, the deep learning based cardiac EP model personalization can be performed in real-time as medical images and EP measurements of the patient are received. Current results indicate that the deep learning based cardiac EP model personalization outperforms existing techniques by high margins in estimating the conduction velocities of the heart.

Figure 1:
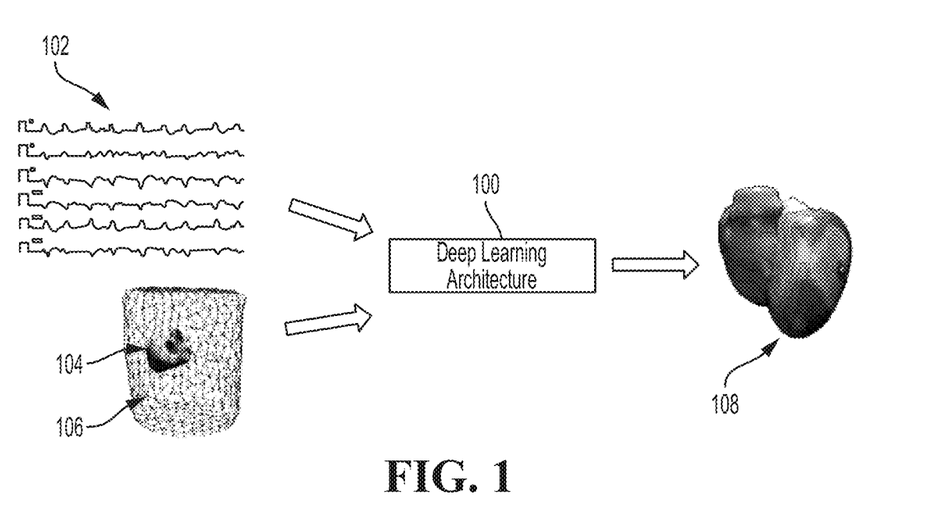
FIG. 1 illustrates a framework for deep learning based cardiac electrophysiology (EP) model personalization according to an embodiment of the present invention.

FIG. 1 illustrates a framework for deep learning based cardiac EP model personalization according to an embodiment of the present invention. As shown in FIG. 1, a trained deep learning architecture 100 is used to personalize a cardiac EP model for a particular patient by estimating patient-specific cardiac EP model parameters for the patient. A measured ECG signal 102 of the patient and patient-specific anatomical models of the heart 104 and the torso 106 of the patient are input to the deep learning architecture 100, and the deep learning architecture 100 estimates spatially varying cardiac EP model parameters, such as conduction velocities, based on the input ECG signal 102 and heart and torso models 104 and 106. The estimated personalized cardiac EP parameters can be visualized by generating a mapping 108 of the personalized cardiac EP model parameters over the patient's heart anatomy (e.g., a color map). The deep learning architecture 100 is a trained deep neural network (DNN) that is trained based on training samples having known ECG signals, heart and torso anatomies, and cardiac EP model parameters (e.g., conduction velocities).

Compared to shallow learning techniques parameterized by few variables, such as support vector machines, deep learning architectures learn hierarchical representations of data through many stacked layers and thus typically require the estimation of many more parameters. As a result, deep learning architectures typically require a larger amount of training data than their shallow alternatives to avoid issues with over-fitting. The deep learning architecture from patient data could be trained from patient data using transmembrane potential measurements (or conduction velocities), body surface potential measurements (e.g., ECG measurements), and cardiac imaging data from which anatomical models of the heart and torso can be extracted. However, the amount of patient data necessary to train the deep learning architecture would be very difficult to obtain due to the fact that transmembrane potential measurements are acquired invasively. Accordingly, in advantageous embodiment of the present invention, a virtual forward-model based generative framework is used to generate synthetic training samples for training the deep learning based architecture.

Figure 2:
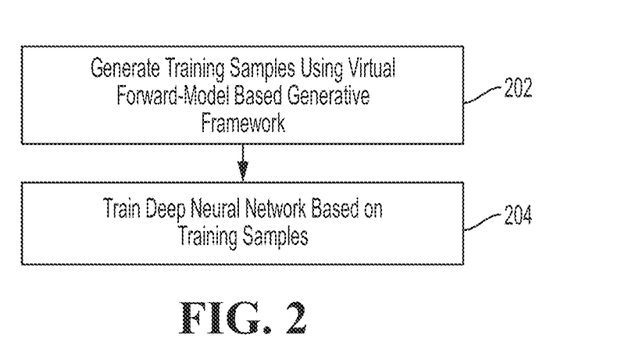
FIG. 2 illustrates a method for training a deep neural network (DNN) for automated cardiac EP model personalization according to an embodiment of the present invention.

FIG. 2 illustrates a method for training a deep neural network (DNN) for automated cardiac EP model personalization according to an embodiment of the present invention. Referring to FIG. 2, at step 202 training samples are generated using a virtual forward-model based generative framework. Starting with training images or anatomical models of the heart and torso extracted from training images, the virtual forward-model based generative framework generates a large number of synthetic training samples. The synthetic training samples generated using the virtual forward-model based generative framework combine realistic cardiac and torso geometries with transmembrane potentials simulated using the forward cardiac EP model with varying randomly selected cardiac EP model parameters. The transmembrane potentials are propagated to obtain body surface potentials, which are then used to compute an ECG trace for each training sample. This framework for generating synthetic training samples is illustrated in greater detail in FIG. 3.

Figure 3:
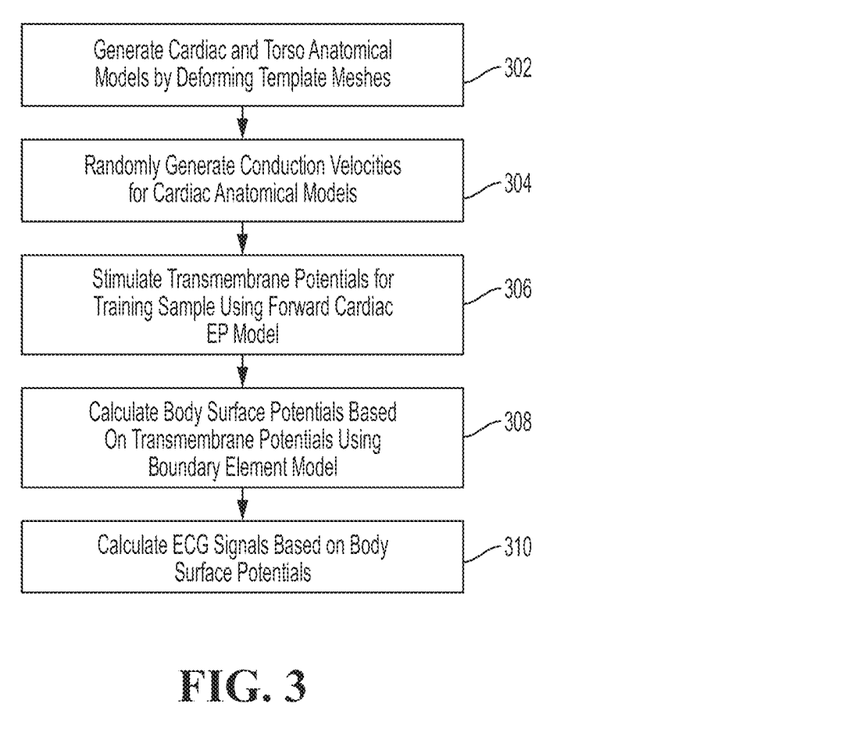
FIG. 3 illustrates a method of generating synthetic training samples according to an embodiment of the present invention.

FIG. 3 illustrates a method of generating synthetic training samples according to an embodiment of the present invention. The method of FIG. 3 can be used to implement step 202 of FIG. 2. Referring to FIG. 3, at step 302, cardiac and torso anatomical models are generated by deforming template meshes. Template cardiac and torso meshes can be generated by segmenting training images. Automated or Semi-automated segmentation techniques may be used to segment the template cardiac and torso meshes. For example, template cardiac meshes can be extracted from training medical images (e.g., CT, MR, etc.) by extracting the heart chambers from the medical images using a Marginal Space Learning (MSL)-based segmentation method, as described in U.S. Pat. No. 7,916,919, issued Mar. 29, 2011, and entitled "System and Method for Segmenting Chambers of a Heart in a Three Dimensional Image", United States Published Patent Application No. 2010/0040272, and United States Published Patent Application No. 2012/0022843, which are incorporated herein by reference in their entirety. The template cardiac meshes may be full heart models including all four chambers or may be models of a portion of the heart, such as only the left and right ventricles. A model of myocardium fiber architecture can be generated for each template cardiac mesh based on the anatomy in the template cardiac mesh using a rule-based method, as described in U.S. Pat. No. 9,463,072, issued Oct. 11, 2016, and entitled "System and Method for Patient Specific Planning and Guidance of Electrophysiology Interventions," which is incorporated herein by reference in its entirety. If scar imaging data (e.g., DE-MRI or CT perfusion) is available scar tissue regions can also be segmented and added to the template cardiac meshes. The template torso meshes can be segmented from training medical images using any machine learning based segmentation technique. In a possible implementation, the torso geometry can also be estimated based on pictures from a camera, such as a 3D camera positioned above a table of a medical image acquisition device.

A number of synthetic cardiac meshes are generated from each template cardiac mesh by randomly deforming the cardiac mesh. In a possible implementation, affine parameters (e.g., location, orientation, and scale) of each template cardiac mesh can all be randomly perturbed within a range of realistic parameters, with each set of randomly perturbed parameters corresponding to a respective synthetic cardiac geometry. However, the present invention is not limited to and specific parameterization, and a more detailed parameterization of the myocardium or different deformation models may be used as well. The template fiber architecture for each template cardiac mesh is also deformed resulting in each synthetic cardiac mesh having a different fiber orientation. Scar addition and scar tissue locations in the synthetic cardiac meshes can also be determined randomly. The template torso meshes are also deformed to generate synthetic meshes having varying torso geometries. For example, similar to the deformation of template cardiac meshes, the template torso meshes can be deformed by randomly perturbing parameters defining a size and shape of the torso within a range of realistic parameters.

At step 304, conduction velocities are randomly generated for the cardiac anatomical models. For a given cardiac mesh, conduction velocities are randomly sampled from a predetermined range of realistic values and assigned to regions of the cardiac mesh. This is performed a large number of times for each of the synthetic cardiac meshes, such that a large number of different realistic synthetic training samples are generated from each of the synthetic cardiac meshes. This can also be performed multiple times for the original template cardiac meshes to generate additional training samples. In an advantageous embodiment, randomly generated conduction velocities for the myocardium, left ventricle, and right ventricle, denoted as $c_{myo}$, $c_{lv}$, and $c_{rv}$, respectively, are assigned. In an exemplary implementation, N (e.g., N=500) different $c_{myo}$, $c_{lv}$, $c_{rv}$ triplets are randomly sampled for each generated cardiac model using the parameter ranges $c_{myo} \in$ [50,1000] and $c_{lv}$, $c_{rv} \in$ [50,4000]. Scar tissue can be assigned a conduction velocity of zero.

At step 306, transmembrane potentials are simulated for each training sample using a forward cardiac EP model. The forward cardiac EP model simulates transmembrane potential for each training sample based on the cardiac anatomical model (cardiac mesh) and the conduction velocities generated for that training sample. In an advantageous embodiment, an Eikonal model can be used to simulate the transmembrane potentials. Eikonal models are simpler in nature as compared to cellular models and they only consider electrical muscle activation making them faster to compute. It is to be understood however, that the method can be similarly applied using other types of cardiac EP models as well.

In an exemplary embodiment, the Lattice-Boltzmann Method for Electrophysiology (LBM-EP) can be used to simulate the transmembrane potentials for each training sample. A Cartesian grid domain for electrophysiology computations is calculated using the anatomical cardiac model. A Cartesian grid, usually with uniform grid spacing but also possibly with unequal and spatially varying spacing, is first generated in a bounding box surrounding the anatomical heart model. Grid spacing can be defined by the user or fixed in the system. A level-set representation is then calculated from the patient-specific anatomical mesh as follows. For every node x of the grid, the shortest distance to the anatomical model mesh is calculated, and assigned to that node. In an advantageous implementation, nodes inside the myocardium are defined by positive distances, and nodes not inside the myocardium are defined by negative distances. The opposite convention can be utilized as well without any modification. Nodes at myocardium, endocardia, and epicardium are tagged as such, as well as septal nodes. Available scars and border zones are also reported in the domain through additional level-set information. Fiber orientation f(x) are mapped to each node using rasterization techniques or are recomputed from the mapped endocardial and epicardial zones directly. A conductivity/diffusion coefficient c(x) and an action potential duration APD(x) is assigned to every myocardial node x of the Cartesian grid. The conduction velocities generated in step 304 provide the conductivity/diffusion coefficients c(x) for each training sample. Cell model parameters can also be mapped spatially at each node.

The cardiac electrophysiology can be simulated by calculating the transmembrane potential at each node within the myocardium using the Lattice-Boltzmann Method for Electrophysiology (LBM-EP) to solve a cardiac electrophysiology model at each node. The cardiac electrophysiology model calculates the variation of the transmembrane potential v(x,t) over time according to the mono-domain equation:

$$\frac{dv(x, t)}{dt} = R(x, t) + \nabla \cdot c(x)D(x)\nabla v(x, t), \quad (1)$$

where R(x,t) is a reaction term describing the cellular mechanisms giving rise to the action potential, c(x) is the local conductivity (conduction velocity) or diffusivity, D(x) is the anisotropy (transverse isotropy) matrix defined by $(1-\rho)f(x)f(x)^T + \rho \text{Id}$, $\rho$ being the ratio between the cross-fiber diffusivity and the fiber diffusivity (typically $\rho$=0.11-0.25). It is also possible to use orthotropic or fully anisotropic tensors D(x) for improved characterization of the fiber architecture.

The choice of the reaction term R(x,t) depends on the cellular model of cardiac electrophysiology that is used. The method disclosed herein is modular in that it can handle any standard mono-domain models, such as, but not limited to the "Mitchell-Schaeffer model" proposed in Mitchell et al., "A Two-Current Model for the Dynamics of Cardiac Membrane", *Bulletin of Mathematical Biology*, 65(5):767-793, 2003, or the model proposed in Ten Tusscher, et al., "Cell Model for Efficient Simulation of Wave Propagation in Human Ventricular Tissue Under Normal and Pathological Conditions", *Physics in Medicine and Biology*, 51, pp 6141, 2006. For the Mitchell-Schaeffer model for instance, we have:

$$R(x, t) = \frac{h(x, t)v^2(x, t)(1 - v(x, t))}{\tau_{in}} - \frac{v(x, t)}{\tau_{out}} + J_{stim}(x). \quad (2)$$

In this equation, $J_{stim}(x)$ is an external stimulus current, which can be kept at 0 for simulating the transmembrane potentials for the training sampled. In Equation (2), h(x,t) is a gating variable that controls the state of the ion channels according to the following ordinary differential equation:

$$\frac{dh(x, t)}{dt} = \begin{cases} \frac{1 - h(x, t)}{\tau_{open}} & \text{if } v(x, t) < v_{gate} \\ \frac{-h(x, t)}{\tau_{close}} & \text{otherwise} \end{cases}$$

$v_{gate}$ is a potential threshold, and $\tau_{in}$, $\tau_{out}$, $\tau_{open}$, and $\tau_{close}$ are parameters controlling the shape of the action potential and the restitution curve. The maximum action potential duration APD(x) is directly related to $T_{close}(x)$ according to the formula $APD_{max}(x) = \tau_{close}(x) \ln(\tau_{out}/(4\tau_{in}))$. In possible embodiments of the present invention, personalized values for only c(x), only $\tau_{close}(x)/APD(x)$, or both c(x) and $\tau_{close}(x)/APD(x)$ are estimated, and the other parameters are kept constant to their default (i.e. nominal) values. However, it is possible to estimate other parameters as well.

Equation (1) is solved using the Lattice-Boltzmann method, referred to herein as LBM-EP. LBM-EP is a highly parallelizable algorithm to solve mono-domain electrophysiology equations. The LBM-EP algorithm is described in greater detail in United States Published Patent Application No. 2013/0226542, entitled "Method and System for Fast Patient-Specific Cardiac Electrophysiology Simulations for Therapy Planning and Guidance", which is incorporated herein by reference in its entirety. Contrary to standard finite-element methods, LBM-EP does not explicitly solve the reaction-diffusion equation but rather computes the "movement" of particles on a Cartesian grid, from which the reaction-diffusion behavior emerges. The particles can move according to fixed directions (or connectivities), with a certain probability. The algorithm includes two node-wise steps: streaming, which makes the particle jump from one node to another; and collision, which takes care of mass preservation and boundary conditions. It can be mathematically shown that this simple algorithm reproduces dynamics of the reaction-diffusion equation. In order to compute the cardiac electrophysiology using LBM-EP, domain boundaries are represented as level-sets and tissue anisotropy is modeled. Since the method is node-wise, the algorithm is highly parallelizable. In an advantageous embodiment, the method can be implemented on a graphics processing unit (GPU), which enables near real-time and accurate cardiac electrophysiology computation during an intervention. In sinus rhythm, the electrocardiography model is computed with periodic stimulus at the septum to mimic the fast conducting His bundle. It should be noted that since the framework relies on Cartesian grids, it is relatively simple to add more structural information in the model. For instance, Purkinje fibers, if available, can be added directly into the domain through rasterization. The His bundle and other electrophysiology bundles can be integrated similarly.

At step 308, body surface potentials for the training samples are calculated based on the transmembrane potentials and the torso anatomical model using a boundary element model. For each training sample, the simulated transmembrane potentials are propagated to the torso mesh using a boundary element method (BEM). An extra-cellular potential $\phi_e$ is calculated at each node of the computational domain based on the simulated transmembrane potential v(x,t) using a closed-form expression ($\Omega$ defines the computational domain; $|\Omega|$ is the number of elements therein):

$$\phi_e(x, t) = \frac{\lambda}{1 + \lambda} \frac{1}{|\Omega|} \int_\Omega [v(y, t) - v(x, t)] dy, \quad (3)$$

where $\lambda$ is a constant diffusion anisotropy ratio, $\lambda = D_i(x)/D_e(x)$, and $D_i$ and $D_e$ are intra- and extra-cellular diffusivity tensors, respectively. The extra-cellular potential $\phi_e$ is then mapped back to the epicardium surface mesh using tri-linear interpolation. The extra-cellular potentials are then projected onto the torso surface mesh using BEM. The potential $\phi(x)$ at any point x of the thoracic domain (torso surface mesh) can be calculated as:

$$\phi(x) = \frac{1}{4\pi} \int_{S_B} \phi_b \frac{r \cdot n}{\|r\|^3} dS_B - \frac{1}{4\pi} \int_{S_H} \left[ \phi_e \frac{r \cdot n}{\|r\|^3} + \frac{\nabla \phi_e \cdot n}{\|r\|} \right] dS_H, \quad (4)$$

where r is the vector defined by x and the integration point n, while $S_B$ and $S_H$ are the torso and epicardium surfaces, respectively. The body surface potential at the torso, $\phi_b$, can be expressed as a function of the extra-cellular potential $\phi_e$, which allows the potential to be calculated at any point on the torso. According to a possible implementation, the body surface potential $\phi_b$ can be calculated for each vertex on the torso mesh. In another possible implementation, the body surface potential $\phi_b$ may be calculated only for vertices on the torso mesh corresponding to the locations of electrodes used to acquire ECG signals (e.g., 12 lead ECG).

At step 308, ECG signals are calculated for the training samples based on the body surface potentials. For each training sample, an ECG signal is calculated using the body surface potentials calculated at locations on the torso mesh corresponding to locations at which electrodes would be placed to measure ECG. The body surface potentials at all standard ECG lead locations (e.g., 12 lead ECG) are estimated, and used to generate simulated ECG signals. In an exemplary implementation, full 12 lead ECG signals can be generated and used to train the DNN, but in other possible implementations partial ECG signals can also be used to train the DNN.

Figure 4:
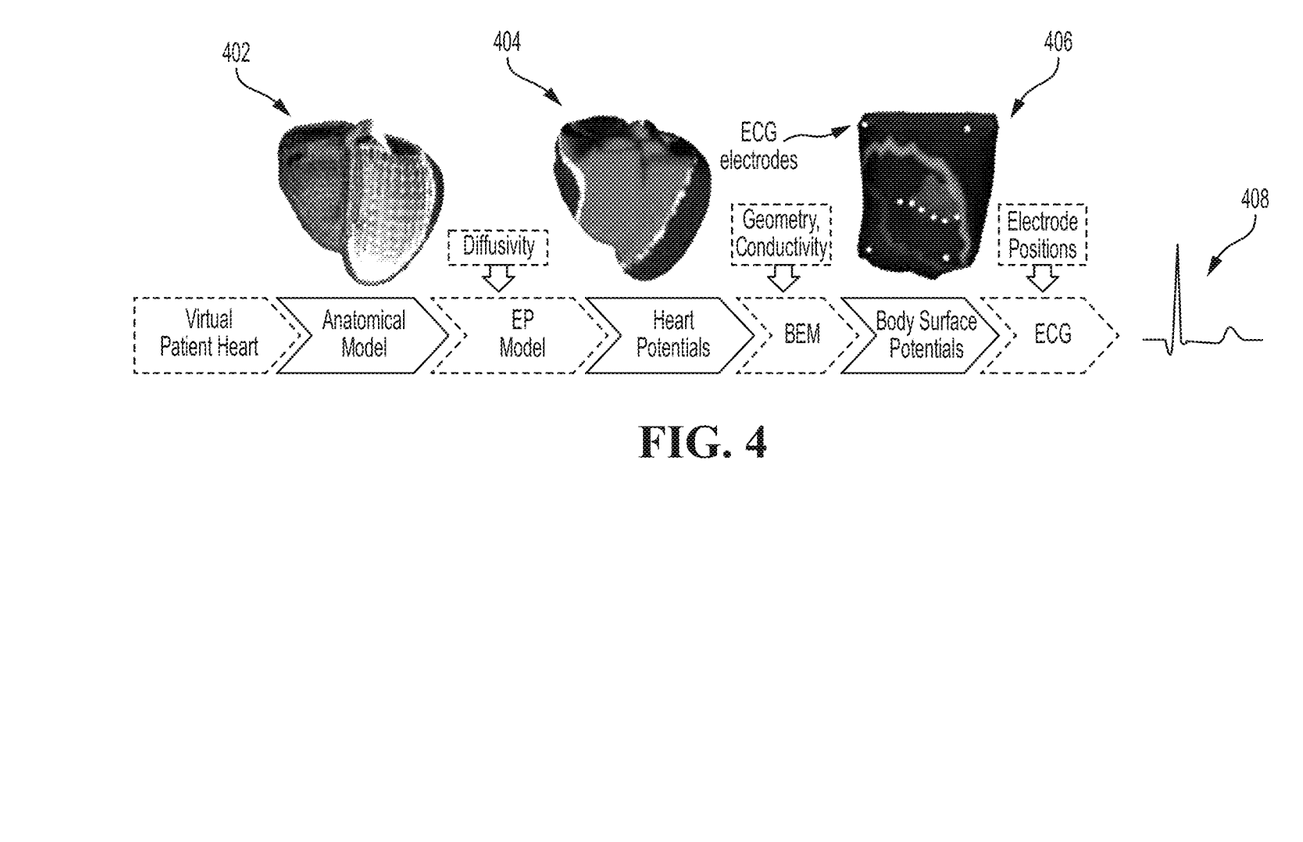
FIG. 4 illustrates generation of a synthetic training sample using the method of FIG. 3.

FIG. 4 illustrates generation of a synthetic training sample using the method of FIG. 3. As shown in FIG. 4, starting with a virtual patient heart template mesh extracted from medical image data, a synthetic anatomical cardiac model is generated by deforming the template heart mesh. An exemplary anatomical cardiac model 402 is shown in FIG. 4. A torso anatomical model is also generated by deforming a template torso model. Conductivity/diffusivity parameters (e.g., conduction velocities) of a computational cardiac EP model are randomly generated and heart potentials (transmembrane potentials) are simulated using the computational cardiac EP model. An exemplary map 404 of simulated transmembrane potentials on the cardiac anatomical model is shown in FIG. 4. A boundary element method (BEM) is then used to propagate the simulated transmembrane potentials to body surface potentials on the torso anatomical model based on the geometry of the cardiac and torso models and the extra-cellular conductivity/diffusivity. An exemplary map 406 of body surface potentials on the torso anatomical model is shown in FIG. 4. The map 406 of body surface potentials also shows ECG electrode locations. The electrode positions are used to calculate an ECG signal. An exemplary ECG signal 408 is shown in FIG. 4. The method of FIG. 3 is used to generate a large number of realistic synthetic training samples, and each training sample has known cardiac and torso geometries, conductivity/diffusivity parameters (e.g., conduction velocities), transmembrane potentials, body surface potentials and ECG signals.

Figure 5:
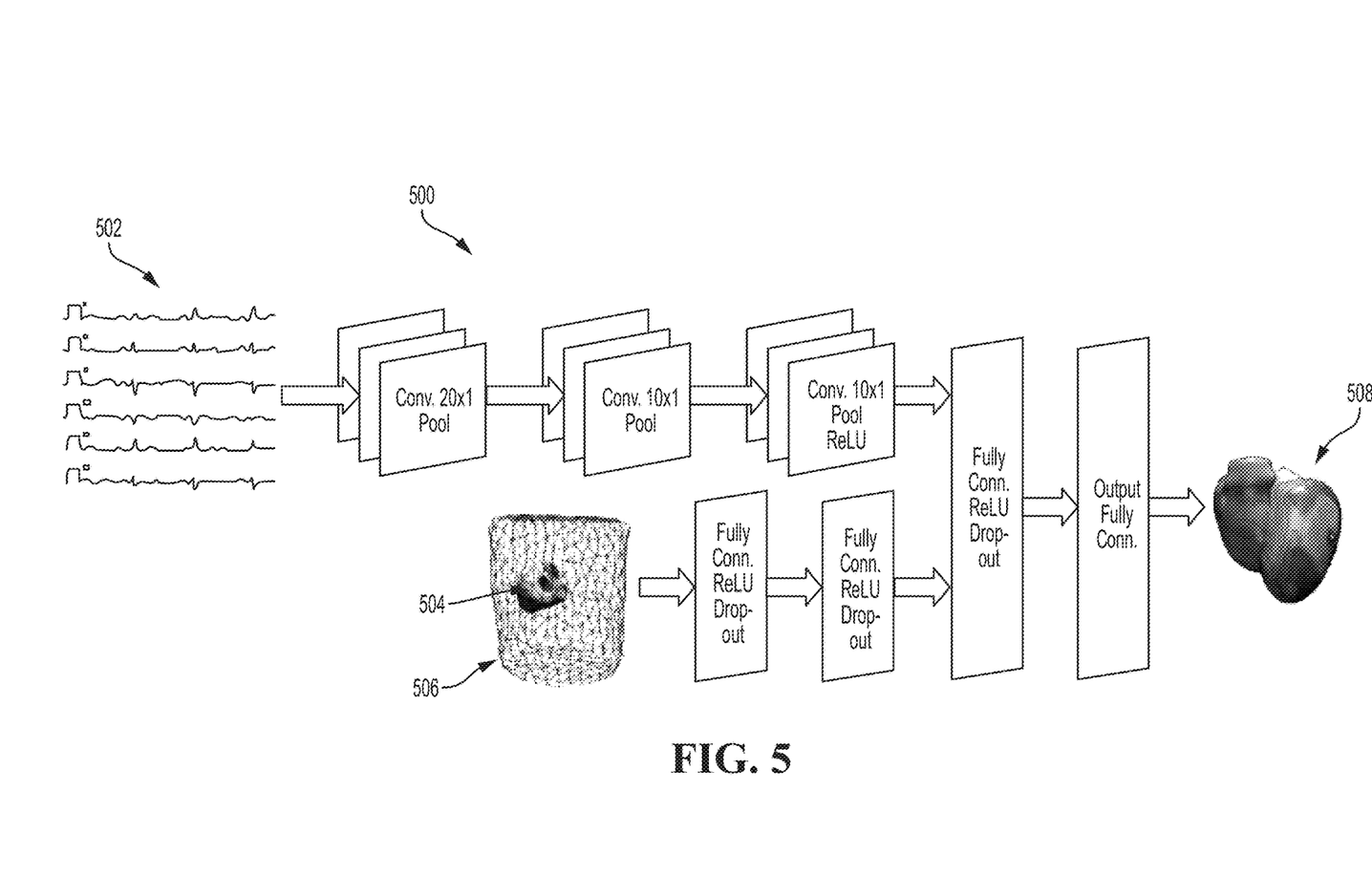
FIG. 5 illustrates an architecture of a DNN for cardiac EP model personalization according to an embodiment of the present invention.

Returning to FIG. 2, at step 204 a deep neural network (DNN) is trained based on the training samples. FIG. 5 illustrates an architecture of a DNN for cardiac EP model personalization according to an embodiment of the present invention. As illustrated in FIG. 5, the DNN 500 accepts three inputs: complete ECG traces 502, cardiac geometry 504, and torso geometry 506. The DNN 500 outputs the estimated model parameters, such as conductivity or diffusivity parameters (e.g., conduction velocities). In FIG. 5, the output conduction velocities are visualized as a color map 508 on the anatomical cardiac model. The inputs to the DNN 500 of FIG. 5 are fed in parallel in two groups, and they are processed in parallel layers until they are merged in a fully connected layer. In doing so, the DNN 500 extracts meaningful representations from different input types (i.e., ECG 502 and cardiac and torso geometry 504 and 506) representing distinct concepts. In the embodiment of FIG. 5, the ECG traces 502 are fed into a 3-layer convolutional framework where each trace is represented by a separate channel. The convolutional kernels are 1-dimensional and their widths can be adjusted to maximize performance. Each convolutional layer is followed by a max-pooling layer that reduces the output size of the convolutional layer. The cardiac and torso geometries 504 and 506 are fed into fully connected layers that are coupled by drop-out layers. The drop-out layers prevent over fitting of the DNN 500 to the geometries of the training set. The drop-out layers are then followed by rectified linear unit (ReLU) layers. The output of ECG layers are reshaped and then merged with the output of the geometry layers in a fully connected layer, which is followed by the output layer. The output layer is a fully connected layer that outputs the personalized cardiac EP model parameters (e.g., conduction velocities). It is to be understood that the architecture of the DNN 500 shown in FIG. 5 can be used in an advantageous embodiment, the present invention is not limited to this specific architecture and other deep learning architectures can be used as well.

In order to train the DNN, the ECG traces and the cardiac and torso geometries of the training samples are input to the DNN and weights are learned for the layers of the DNN to minimize a loss function (e.g., a Euclidean loss function) that measures a distance between the cardiac EP model parameters estimated by the DNN and the known cardiac EP model parameters of the training samples over all of the training samples. For example, gradient descent and back-propagation can be used to learn the DNN weights that minimize the loss function. Once the DNN is trained the trained DNN can be stored, for example on a memory or storage of a computer system. The trained DNN can then be used to directly estimate cardiac EP parameters corresponding to cardiac tissue properties from measured ECG traces of a patient and cardiac and torso geometries extracted from medical images of a patient, both to generate a mapping of the cardiac tissue properties for diagnostic purposes and to personalize a cardiac EP model for cardiac EP simulations.

Figure 6:
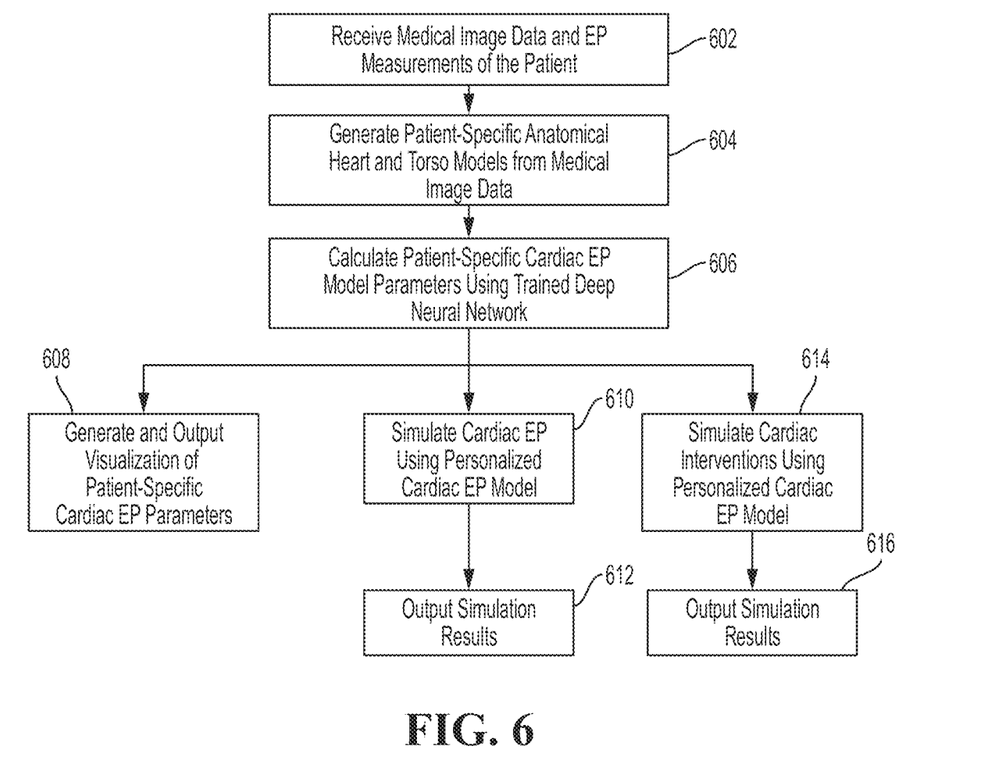
FIG. 6 illustrates a method of personalizing a cardiac EP model for a patient according to an embodiment of the present invention.

FIG. 6 illustrates a method of personalizing a cardiac EP model for a patient according to an embodiment of the present invention. The method of FIG. 6 estimates patient-specific spatially varying parameters of a cardiac EP model that correspond to cardiac tissue properties, such as conductivity/diffusivity values (conduction velocities). These spatially varying cardiac tissue properties provide valuable diagnostic information. In addition, the personalized cardiac EP model can be used to simulate patient-specific cardiac EP of the patient and to simulate the effect cardiac interventions, such as CRT and radio-frequency ablation, on the patient.

At step 602, medical image data and EP measurements of the patient are received. The medical image data can be acquired using any type of medical imaging modality, such as computed tomography (CT), three-dimensional rotational angiography, magnetic resonance imaging (MRI), ultrasound (US), etc. In an advantageous implementation, the medical image data includes three dimensional (3D) medical image data including at least a cardiac region of the patient. The medical image data may also include 3D medical image data including a torso of the patient. The medical image data can be received directly from an image acquisition device, such as a CT scanner, a C-arm image-acquisition device, an MRI scanner, or an US scanner, as the medical image data is acquired by the image acquisition device. Alternatively, the medical image data can be received by loading previously acquired medical image data of the patient or can be received via an electronic transmission from a remote computer system. In an advantageous embodiment, the EP measurements are non-invasive EP measurements, such as ECG traces (12 lead, standard, etc.) or dense body surface potential measurements (e.g., body surface mapping (BSM)). Any number and positions of electrodes on the torso surface can be used to acquire the non-invasive EP measurements. In an alternative embodiment, the EP measurements can be invasive intra-cardiac catheter based EP measurements.

At step 604, patient-specific anatomical heart and torso models are generated from the medical image data. In order to generate the patient-specific anatomical heart model, a patient-specific heart morphology model is extracted from the medical image data. The patient-specific heart morphology model can be a comprehensive geometrical model that represents the patient-specific heart morphology. In an advantageous embodiment, the patient-specific heart morphology model includes individual anatomical models representing the morphology of various heart components. The models are highly modular and can be customized depending on the application. The complete heart model can comprise the left ventricle (LV), left atrium (LA), left outflow tract, aortic root, pulmonary veins, right ventricle (RV), right atrium (RA), right outflow tract, RV neck, and veins. Papillaries and trabeculae can also be obtained, from CT images for instance. Each of these components can be used individually or jointly according to data availability and clinical application. In an exemplary embodiment, the LV and RV anatomical models estimated from the medical image data are used. In a possible implementation, only the LV and RV are explicitly modeled. In another possible implementation, models for all of the heart chambers are extracted. It is also possible that the comprehensive model including all of the heart components is extracted. The modularity of this framework enables using images in which only part of the anatomy is visible.

The anatomical model for each heart component can be extracted individually. Although this can be done manually through interactive contouring, in advantageous implementations automatic or semi-automatic approaches are employed to extract the heart components. For instance, for each heart chamber, the heart chamber segmentation can be formulated as a two-step learning problem: anatomical structure localization and boundary delineation. In an advantageous embodiment, marginal space learning (MSL) can be used to apply machine learning to 3D object detection. The idea of MSL is not to learn a monolithic classifier directly in the full similarity transformation parameter space but to incrementally learn classifiers on marginal spaces. In particular, the detection of each heart chamber can be split into three problems: position estimation, position-orientation estimation, and position-orientation-scale estimation. A separate classifier is trained based on annotated training data for each of these estimation problems. Each classifier can be a probabilistic boosting tree (PBT) classifier trained based on annotated training data. The classifiers in the lower dimensional marginal spaces are used to prune the searching space efficiently. This object localization stage results in an estimated transformation (position, orientation, and scale) of the object (e.g., heart chamber).

After automatic object localization, the mean shape model of the object is aligned with the estimated transformation to get a rough estimate of the object shape. The shape is then deformed locally to fit the object boundary. Active shape models (ASM) can be used to deform an initial estimate of a non-rigid shape under the guidance of the image evidence and the shape prior. However, a non-learning based generic boundary detector, as used in conventional ASM applications, does not work effectively in heart chamber deformation due to the complex background and weak edges. Instead, a learning based boundary detector can be used to exploit more image evidences to achieve a robust boundary detection. Additional details regarding MSL-based heart chamber segmentation are described in U.S. Pat. No. 7,916,919, issued Mar. 29, 2011, and entitled "System and Method for Segmenting Chambers of a Heart in a Three Dimensional Image", United States Published Patent Application No. 2010/0040272, and United States Published Patent Application No. 2012/0022843, which are incorporated herein by reference.

The patient-specific heart morphology model is fused into a single volumetric mesh representation and surface elements of the mesh are tagged into surface zones. For example, in the case in which the anatomical heart model includes only the LV and RV, the patient-specific LV and RV anatomical models can be fused into a single anatomical model of the bi-ventricular myocardium. In particular, the LV and RV anatomies are fused into a single volumetric mesh representation, on which vertices are tagged into surface zones (LV endocardium, LV septum, RV endocardium, RV septum) according to the underlying anatomy of the estimated surface models. According to an advantageous embodiment, tetrahedral elements can be used to accurately represent the details of the volumetric bi-ventricular anatomy. Spatial information, such as scars, grey zones, and fibrosis can be identified in images, such as late enhancement MRI. For example, the spatial information may be automatically identified using trained classifiers or may be manually identified by a clinician. The spatial information is mapped onto the volumetric mesh representing the bi-ventricular myocardium. This information is important to simulate electrical delays, electrical waves around scars, for instance, wave-reentry assessment and correctly capture impaired cardiac mechanics due to ill-functioning or dead cells.

A model of fiber orientation can be automatically calculated based on the patient-specific geometry. In an advantageous implementation, the model of fiber orientation can be automatically calculated using a rule-based approach. A generic model of myocardium fiber architecture that includes fiber and fiber sheets is computed. A rule-based strategy is followed to generate the fiber architecture to cover the entire bi-ventricular myocardium from apex to valves. Below the basal plane, which is identified automatically using point correspondences of the initial triangulations of the anatomical model, the fiber elevation angle $\alpha$, i.e. their angle with respect to the short axis plane, varies linearly across the myocardium, e.g., from −70 on the epicardium to +70 on the endocardium (values that can be defined by the user). Similarly, the sheet direction, which is defined by the angle $\beta$ with respect to the outward transmural axis, varies transmurally, e.g., from +45 on the epicardium to −45 on the endocardium (values that can be defined by the user). $\alpha$ and $\beta$ are computed for each point of the volumetric bi-ventricular myocardium mesh between the apex and basal plane based on the geodesic distance to the endocardia and epicardia identified by the facet tags: $\alpha = (d_{epi}\alpha_{endo} + d_{endo}\alpha_{epi})/(d_{endo} + d_{epi})$, where $d_{epi}$, $d_{endo}$, $\alpha_{epi}$, $\alpha_{endo}$ and are the distances and angles at the endocardium and epicardium, respectively. The fiber and sheet orientations are then fixed around each valve. In particular, fibers are longitudinal around the aortic valve and tangential around the mitral, tricuspid, and pulmonary valves, and sheet normals are oriented towards the barycenter of the valves. The local orthonormal basis is then interpolated from the basal plane to the valve, first by following the myocardium surface, then throughout the myocardium thickness. In another embodiment, when MRI diffusion tensor imaging (DTI) is available, the fibers can be directly measured in-vivo, in the patient, using the MRI diffusion tensor imaging. In another embodiment, an atlas of cardiac fibers could be employed to register the fibers to the anatomical model. Additional details regarding generating the patient-specific anatomical heart model are described in U.S. Published Patent Application No. 2013/0197881 and U.S. Published Patent Application No. 2015/0042464, which are incorporated herein in their entirety by reference.

In addition to the patient-specific anatomical heart model, a detailed torso surface model of the patient can be extracted from the medical image data. For example, the detailed torso surface model can be extracted by automatically segmenting the patient's torso geometry from the medical image data using machine learning segmentation techniques.

At step 606, patient-specific cardiac EP model parameters are calculated using a trained DNN. The DNN calculates spatially varying cardiac EP model parameters, such as conduction velocities, at various locations in the anatomical heart model based on the EP measurements (e.g., ECG) of the patient and the cardiac and torso geometries in the patient-specific anatomical heart and torso models. In an exemplary implementation, the trained DNN estimates conduction velocity values for the myocardium $c_{myo}$, the left ventricle $c_{lv}$, and the right ventricle $c_{rv}$. Alternatively, the trained DNN can estimate conduction velocities for smaller regions in the patient-specific anatomical heart model or even for individual points of the patient-specific anatomical heart model. In an advantageous embodiment, the DNN 500 of FIG. 5 may be used to calculate the patient-specific cardiac EP model parameters, such as conduction velocities.

The patient-specific cardiac EP model parameters calculated using the trained DNN correspond to electrical cardiac tissue properties of the patient, which provide valuable diagnostic information. In addition, once the cardiac electrophysiology model is personalized with patient-specific parameters, this patient-specific cardiac EP model is generative, and can be used to virtually simulate the patient's cardiac EP and/or any electrophysiological intervention without actual testing on the patient. Once the patient-specific cardiac EP parameters are calculated using the trained DNN in step 606, the method can proceed to step 608, step 610, and/or step 614. The method may proceed to any or all of steps 608, 610, and 614.

At step 608, a visualization of the patient-specific cardiac EP parameters is generated and output. For example, the spatially varying patient-specific cardiac, which correspond to electrical cardiac tissue properties, can be visualized by overlaying a color map in which different colors represent different values for the patient-specific cardiac EP parameters on the patient-specific anatomical heart model or the segmented heart structures in the medical images. This visualization of the patient-specific cardiac parameters can be output by displaying the visualization on a display device of a computer system or transmitting the visualization to a remote computer device to be displayed by the remote computer device.

At step 610, cardiac EP of the patient is simulated using the personalized cardiac EP model. The cardiac EP model described above in connection with FIG. 3 can be used to perform the cardiac EP simulation. The cardiac EP model is a computational model that simulates transmembrane potential propagation over the patient-specific anatomical heart model. As the personalized cardiac EP model is personalized with patient-specific cardiac EP model parameters, such as conductivity/diffusivity parameters, the personalized cardiac EP model simulates patient-specific transmembrane potentials for the patient. The patient-specific simulation of transmembrane potentials provides valuable diagnostic information for the patient. In addition, the simulated transmembrane potentials can be propagated to calculate body surface potentials at points on the patient-specific anatomical torso model, which can be used to generate a simulated ECG signal for the patient.

At step 612, the simulation results from the cardiac EP simulation in step 610 are output. The simulated transmembrane potentials can be visualized by generating a color map in which the colors correspond to the simulated transmembrane potential values on the extracted patient-specific anatomical heart model. A map of activation times of the simulated transmembrane potentials can be similarly visualized. Simulated body surface potentials can be visualized by overlaying a color map representing the simulate body surface potentials on the patient-specific anatomical torso model. These visualizations can be output by being displayed on a display device of a computer system or by being transmitted to a remote computer device for display on the remote computer device. The simulated ECG signal can be visualized by generating ECG traces, which can be displayed on a display device of a computer system or transmitted to a remote computer device for display on the remote computer device. The simulated ECG traces can be compared to the measured ECG traces to check the accuracy of the estimated patient-specific parameters of the cardiac EP model.

At step 614, one or more cardiac electrophysiological interventions are simulated using the personalized cardiac EP model. Once the cardiac electrophysiology model is personalized with patient-specific parameters, this patient-specific cardiac EP model is generative, and can be used to virtually simulate any electrophysiological intervention without actual testing on the patient. Intervention planning can be performed by simulating different virtual interventions using the patient-specific cardiac EP model. Since the system is generative, cardiac electrophysiology can be computed under different virtual interventions. As a result, several therapeutic scenarios can be tested in-silico. The virtual electrophysiological interventions, such as CRT or radiofrequency ablation procedures, can be used for pre-operative planning or intra-operative guidance. For each virtual electrophysiological intervention, the transmembrane potentials, extra-cellular potentials, body surface potentials, and simulated ECG signal can be simulated and displayed. Dynamic potential maps can be visualized. In order to perform a virtual intervention involving a pacing therapy, such as CRT, one or several virtual pacing electrode locations can be received. Since the system is generative, the user (e.g., physician) can select one or more locations to virtually pace the heart, given the patient-specific cardiac EP model parameters (e.g., conductivity/diffusivity c(x) and/or the action potential duration APD(x)). The user can input one or several spatial locations for a virtual pacing electrode, for example using an input device, such as a mouse, touch screen, etc., of a computer system to select a spatial location on the anatomical heart model or one of the cardiac electrocardiography maps generated by the patient-specific cardiac EP model. In an alternative implementation, systematic virtual pacing may be automatically applied by rasterizing the model, in order to identify optimal pacing locations. In particular, a sampling scheme can be used to automatically select virtual pacing locations, and a virtual electrophysiological intervention can be performed for each pacing location. The cardiac electrophysiology is then calculated using the patient-specific cardiac EP model. In particular, a stimulus current $J_{stim}$ is added to the patient-specific cardiac EP model at the locations of the virtual pacing catheter and the cardiac electrophysiology is simulated over a period of time. The strength and timing of the stimulus current can depend on a pacing protocol being tested. Each pacing electrode can pace at the same or different pacing times, according to the user choice or the pacing protocol being tested.

Such simulated interventions can be similarly performed for ablation therapies by selecting one or more ablation target locations, either by a user or automatically by rasterizing the model in order to identify optimal ablation locations. Ablation is then simulated by locally setting the tissue diffusivity to 0 to mimic the ablated lesion, or by using a coupled bio heat model similar to United States Patent Publication No. 2014/0136174, which is incorporated herein by reference in its entirety.

The outcome of several different virtual interventions, performed interactively or automatically by placing leads or selecting ablation locations at various locations on the myocardium tissue, can be quantitatively compared before implementing them. In addition, simulations of the interventions can be performed using several different pacing protocols or ablation protocols in order to determine the optimal pacing/ablation protocol for the intervention.

At step 614, the simulation results of the simulated cardiac electrophysiological are output. For example, the simulation results can be output by visualizing dynamic electrophysiology maps (e.g., dynamic potential maps) of the simulated transmembrane potentials on the patient-specific anatomical heart model and/or the body surface potentials on the patient-specific torso model and displaying these maps on a display device or transmitting these maps to a remote device for display on the remote device. For example, the spatially varying transmembrane or body surface potentials can be visualized by color coding the mesh of the patient's anatomy. Other electrophysiological maps, such as a 3D map of depolarization times, and a 3D map of repolarization times, can also be visualized and displayed. In addition, simulated ECG signals resulting from the simulated interventions can displayed on a display device or transmitted to a remote device for display on the remote device. The output simulation results can be used to plan or guide a cardiac intervention procedure. For example, the simulated cardiac electrophysiology can be used to choose one or several locations and timing of a pacing electrode or ablation catheter. Further, the generation and display of the simulated ECG signals for the simulated interventions allows evaluation of electrophysiological interventions to be achieved in-silico, as ECG-based measurements provide clinically relevant indicators of the success of the procedures.

The above described methods were tested with ECG simulations obtained using patient data. In particular, 86 patients with available torso and cardiac geometries were used to generate training samples. For each patient in the training set, 500 ECG simulations with conduction velocity values for the myocardium $c_{myo}$, left ventricle $c_{iv}$, and right ventricle $c_{rv}$ randomly sampled using the parameter ranges $c_{myo} \in [50,1000]$ and $c_{iv}, c_{rv} \in [50,4000]$. Test data was similarly generated using 4 patients and 500 ECG simulations each. After the DNN was trained using the training samples, the trained DNN was used to calculate the values for $c_{myo}$, $c_{iv}$, and $c_{rv}$ for the test cases. The same test cases were also used in assessing the performance of estimating the conductivities using conventional inverse optimization. The estimate values for both methods are compared with the ground truth values and the absolute mean and median errors are shown in Table 1. As shown in Table 1, the deep learning based method (Proposed) outperformed the inverse optimization approach (Inverse Opt) by high margins, yielding much more reliable estimates of the conduction velocities.

TABLE 1

|  | Proposed (mean) | Proposed (Median) | Inverse Opt (Mean) | Inverse Opt (Median) |
| --- | --- | --- | --- | --- |
| $c_{iv}$ | 230 | 188 | 616 | 333 |
| $c_{rv}$ | 142 | 116 | 861 | 580 |
| $c_{myo}$ | 25 | 19 | 111 | 87 |

The performances of the deep learning based method and the inverse optimization approach were also evaluated in the ECG space. In order to do so, the conduction velocities estimated by both methods are used to simulate transmembrane potentials, which are then propagated to body surface potentials to generate simulated ECG signals. The correlation coefficient between each simulated ECG signal and its ground truth is shown in Table 2. As shown in Table 2, the ECG signals generated using the cardiac EP model parameters (conduction velocities) estimated using the deep learning based method (Proposed) correlate much better to their ground truths than those generated using cardiac EP model parameters estimated using inverse optimization (Inverse Opt).

TABLE 2

|  | Proposed (Mean) | Proposed (Median) | Inverse Opt (Mean) | Inverse Opt (Median) |
| --- | --- | --- | --- | --- |
| Test Patient-1 | 0.95 | 0.98 | 0.75 | 0.87 |
| Test Patient-2 | 0.97 | 0.98 | 0.78 | 0.85 |
| Test Patient-3 | 0.92 | 0.95 | 0.84 | 0.9 |
| Test Patient-4 | 0.93 | 0.97 | 0.5 | 0.63 |

In the above described embodiment, a trained DNN calculates patient-specific cardiac EP model parameters based on EP measurements of the patient and cardiac and torso geometries of the patient, which are input to the trained DNN. In an alternative embodiment, the cardiac model personalization using the trained DNN can be performed solely utilizing the EP measurements (e.g., ECG) of the patient, without the presence of the anatomical information of the patient. In this case, only the EP measurements (e.g., ECG) generated for the training samples is used to train the DNN. In a possible implementation, the DNN can be trained to estimate the patient-specific cardiac EP parameters based on partial ECG traces instead of requiring full ECG traces.

In another possible embodiment, additional information can be input to the DNN along with the EP measurements and cardiac and torso geometries of the patient. For example, the DNN can be trained to consider patient-specific information regarding existing symptoms, clinical history, and/or measurements by an auxiliary device, in addition to the EP measurements and cardiac and torso geometries, when estimating the patient-specific cardiac EP model parameters.

In the above described embodiments, patient-specific conduction cardiac EP parameters are estimated based on EP measurements of a patient using a trained DNN. In an exemplary implementation described above, the cardiac EP parameters are conduction velocities and the EP measurements are ECG signals. In another possible implementation, the EP measurements may be t-wave measurements and the cardiac EP parameters that are estimated are action potential durations. In this case, the trained DNN is trained to calculate spatially varying action potential durations based on t-wave measurements of a patient. In another possible embodiment, both ECG measurements and t-wave measurements of a patient can be acquired and two trained DNNs can be used to personalize a cardiac EP model: a first DNN to estimate patient-specific conduction velocities based on the ECG measurements, and a second DNN to estimate action potential durations based on the t-wave measurements. Alternatively, a single DNN may be trained to input both ECG and t-wave measurements and estimate both patient-specific conduction velocities and patient-specific action potential durations.

In the above described embodiments, the patient-specific torso model is extracted from medical image data of the patient and standard lead locations on the torso are used to generate the simulated ECG signals. In an alternative embodiment, camera-based estimation of torso geometry and lead locations may be performed.

Figure 7:
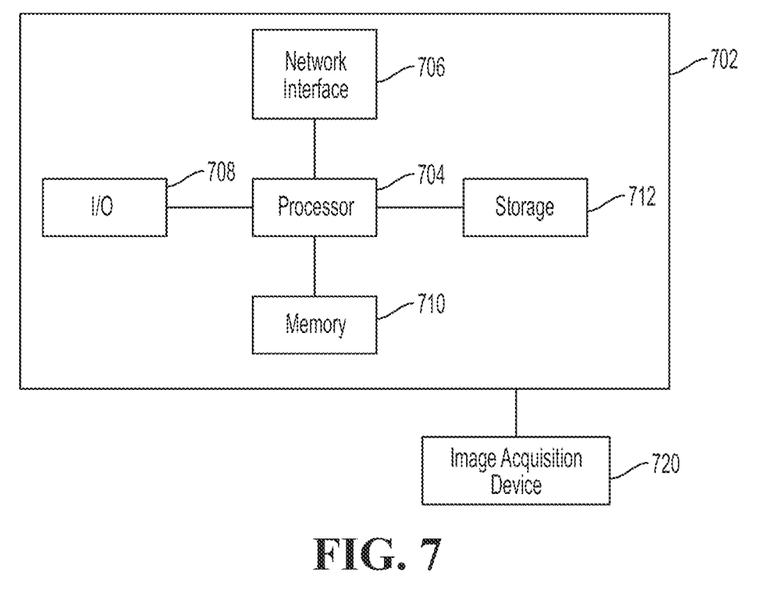
FIG. 7 is a high-level block diagram of a computer capable of implementing the present invention.

The above-described methods for training a DNN, generating training samples, and personalizing a cardiac EP model can be implemented on one or more computers using well-known computer processors, memory units, storage devices, computer software, and other components. A high-level block diagram of such a computer is illustrated in FIG. 7. Computer 702 contains a processor 704, which controls the overall operation of the computer 702 by executing computer program instructions which define such operation. The computer program instructions may be stored in a storage device 712 (e.g., magnetic disk) and loaded into memory 710 when execution of the computer program instructions is desired. Thus, the steps of the methods of FIGS. 2, 3, and 6 may be defined by the computer program instructions stored in the memory 710 and/or storage 712 and controlled by the processor 704 executing the computer program instructions. An image acquisition device 720, such as a CT scanning device, C-arm image acquisition device, MR scanning device, Ultrasound device, etc., can be connected to the computer 702 to input image data to the computer 702. It is possible to implement the image acquisition device 720 and the computer 702 as one device. It is also possible that the image acquisition device 720 and the computer 702 communicate wirelessly through a network. The computer 702 also includes one or more network interfaces 706 for communicating with other devices via a network. The computer 702 also includes other input/output devices 708 that enable user interaction with the computer 702 (e.g., display, keyboard, mouse, speakers, buttons, etc.). One skilled in the art will recognize that an implementation of an actual computer could contain other components as well, and that FIG. 7 is a high level representation of some of the components of such a computer for illustrative purposes.

In one embodiment, the computer that performs one or more of the above described methods may be integrated into a medical image scanner (image acquisition device). In another embodiment, the computer that performs one or more of the above described methods may be a mobile device, such as a smart phone or tablet. In another embodiment, the computer that performs one or more of the above described methods may be part of a patient monitoring system.

In another embodiment, one or more of the above described methods for training a DNN, generating training samples, and/or personalizing a cardiac EP model may be implemented in network-based cloud computing system. In such a network-based cloud computing system, a server communicates with one or more client computers via a network. A client computer may communicate with the server via a network browser application residing and operating on the client computer, for example. A client computer may store data on the server and access the data via the network. A client computer may transmit requests for data, or requests for online services, to the server via the network. The server may perform requested services and provide data to the client computer(s). The server may also transmit data adapted to cause a client computer to perform a specified function, e.g., to perform a calculation, to display specified data on a screen, etc. Certain steps of the above described methods may be performed by a server or by other computers/processors in the network-based cloud-computing system. Certain steps of the above described methods may be performed locally by a client computer in a network-based cloud computing system. The steps of the above described methods may be performed by one or more devices in the network-based cloud-computing system or by a local client computer in any combination. In one embodiment, the trained DNN is stored on a device in the network-based cloud computing system and the calculation of cardiac EP model parameters is performed as a service by a device in the cloud computing system based on patient data uploaded/transmitted to the above cloud computing system from a client computer. For example, the EP measurements and medical image data of the patient can be uploaded to the cloud computing system, and the cloud computing system can extract the patient-specific anatomical heart and torso anatomies and then calculate the patient-specific cardiac EP parameters using the trained DNN. Alternatively, the client computer can extract the patient-specific anatomical heart and torso models and then upload the EP measurements and the extracted heart and torso models to the cloud computing system, which then calculates the patient-specific cardiac EP parameters using the trained DNN. The cloud computing system can transmit the estimated patient-specific cardiac EP parameters and/or visualizations (e.g., color maps) of the cardiac EP parameters back to the client computer. In a possible implementation, the cloud computing system can also perform simulation of cardiac EP for the patient and/or simulation of cardiac interventions for the patient using the personalized cardiac EP model, and transmit the simulation results back to the client device. Alternatively, the simulations of the patient's cardiac EP and/or the cardiac interventions using the personalized model may be performed by the client computer once the patient-specific cardiac EP model parameters are received from the cloud computing system.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method for personalizing a cardiac electrophysiology model for a patient, comprising:
receiving medical image data and an electrocardiography (ECG) trace of the patient;
generating patient-specific anatomical heart and torso models from the medical image data; and
personalizing a computational cardiac electrophysiology model using a trained deep neural network (DNN), wherein the trained DNN 1) receives as input the ECG trace at a first group of layers and the patient-specific anatomical heart and torso models at a second group of layers and 2) merges outputs of the first group of layers and the second group of layers at a third group of layers to generate as output patient-specific values for a parameter of the computational cardiac electrophysiology model, wherein the parameter of the computational cardiac electrophysiology model corresponds to a spatially varying electrical cardiac tissue property.

2. The method of claim 1, further comprising:
generating a visualization of the patient-specific values for the parameter of the computational cardiac electrophysiology model on the patient-specific anatomical heart model.

3. The method of claim 1, further comprising:
simulating transmembrane potentials at a plurality of locations in the patient-specific anatomical heart model using the personalized computational cardiac electrophysiology model.

4. The method of claim 3, further comprising:
calculating body surface potentials at a plurality of locations on the patient-specific anatomical torso model based on the simulated transmembrane potentials; and
generating a simulated ECG signal based on the body surface potentials.

5. The method of claim 4, further comprising:
generating at least one of a visualization of the simulated transmembrane potentials on the patient-specific anatomical heart model or a visualization of the calculated body surface potentials on the patient-specific anatomical torso model.

6. The method of claim 1, further comprising:
simulating one or more cardiac electrophysiological interventions using the personalized computational cardiac electrophysiology model.

7. The method of claim 6, wherein simulating one or more cardiac electrophysiological interventions using the personalized computational cardiac electrophysiology model comprises:
simulating transmembrane potentials at a plurality of locations in the patient-specific anatomical heart model using the personalized computational cardiac electrophysiology model with a stimulus current added at at least one spatial location corresponding to a location of a pacing catheter or an ablation location.

8. The method of claim 7, further comprising:
calculating body surface potentials at a plurality of locations on the patient-specific anatomical torso model based on the simulated transmembrane potentials; and
generating a simulated ECG signal based on the body surface potentials.

9. The method of claim 1, wherein personalizing a computational cardiac electrophysiology model using a trained deep neural network (DNN) comprises:
calculating spatially varying patient-specific conduction velocity values based on the ECG trace of the patient using the trained DNN.

10. The method of claim 1, further comprising receiving t-wave measurements of the patient, and personalizing a computational cardiac electrophysiology model using a trained deep neural network (DNN) comprises:
calculating spatially varying patient-specific action potential duration values based on the t-wave measurements of the patient using the trained DNN.

11. The method of claim 1, wherein the trained DNN is trained using synthetic training samples having known ground truth ECG traces and known ground truth values for the parameter of the computational cardiac electrophysiology model, and each of the synthetic training samples is generated by randomly sampling values for the parameter of the computational cardiac electrophysiology model for a plurality of regions of a cardiac geometry in predetermined ranges for the regions, simulating transmembrane potentials in the cardiac geometry using the computational cardiac electrophysiology with the randomly sampled values for the parameter, propagating the simulated transmembrane potentials to body surface potentials on a torso geometry, and generating an ECG trace based on the body surface potentials.

12. An apparatus for personalizing a cardiac electrophysiology model for a patient, comprising:
a processor; and
a memory storing computer program instructions, which when executed by the processor cause the processor to perform operations comprising:
receiving medical image data and an electrocardiography (ECG) trace of the patient;
generating patient-specific anatomical heart and torso models from the medical image data; and
personalizing a computational cardiac electrophysiology model using a trained deep neural network (DNN), wherein the trained DNN 1) receives as input the ECG trace at a first group of layers and the patient-specific anatomical heart and torso models at a second group of layers and 2) merges outputs of the first group of layers and the second group of layers at a third group of layers to generate as output patient-specific values for a parameter of the computational cardiac electrophysiology model, wherein the parameter of the computational cardiac electrophysiology model corresponds to a spatially varying electrical cardiac tissue property.

13. The apparatus of claim 12, wherein the operations further comprise:
generating a visualization of the patient-specific values for the parameter of the computational cardiac electrophysiology model on the patient-specific anatomical heart model.

14. The apparatus of claim 12, wherein the operations further comprise:
simulating transmembrane potentials at a plurality of locations in the patient-specific anatomical heart model using the personalized computational cardiac electrophysiology model.

15. The apparatus of claim 14, wherein the operations further comprise:
calculating body surface potentials at a plurality of locations on the patient-specific anatomical torso model based on the simulated transmembrane potentials; and
generating a simulated ECG signal based on the body surface potentials.

16. The apparatus of claim 12, wherein the operations further comprise:
    simulating one or more cardiac electrophysiological interventions using the personalized computational cardiac electrophysiology model.

17. The apparatus of claim 12, wherein personalizing a computational cardiac electrophysiology model using a trained deep neural network (DNN) comprises:
    calculating spatially varying patient-specific conduction velocity values based on the ECG trace of the patient using the trained DNN.

18. The apparatus of claim 12, wherein the trained DNN is trained using synthetic training samples having known ground truth ECG traces and known ground truth values for the parameter of the computational cardiac electrophysiology model, and each of the synthetic training samples is generated by randomly sampling values for the parameter of the computational cardiac electrophysiology model for a plurality of regions of a cardiac geometry in predetermined ranges for the regions, simulating transmembrane potentials in the cardiac geometry using the computational cardiac electrophysiology with the randomly sampled values for the parameter, propagating the simulated transmembrane potentials to body surface potentials on a torso geometry, and generating an ECG trace based on the body surface potentials.

19. A non-transitory computer readable medium storing computer program instructions for personalizing a cardiac electrophysiology model for a patient, the computer program instructions when executed by a processor cause the processor to perform operations comprising:
    receiving medical image data and an electrocardiography (ECG) trace of the patient;
    generating patient-specific anatomical heart and torso models from the medical image data; and
    personalizing a computational cardiac electrophysiology model using a trained deep neural network (DNN), wherein the trained DNN 1) receives as input the ECG trace at a first group of layers and the patient-specific anatomical heart and torso models at a second group of layers and 2) merges outputs of the first group of layers and the second group of layers at a third group of layers to generate as output patient-specific values for a parameter of the computational cardiac electrophysiology model, wherein the parameter of the computational cardiac electrophysiology model corresponds to a spatially varying electrical cardiac tissue property.

20. The non-transitory computer readable medium of claim 19, wherein the operations further comprise:
    generating a visualization of the patient-specific values for the parameter of the computational cardiac electrophysiology model on the patient-specific anatomical heart model.

21. The non-transitory computer readable medium of claim 19, wherein the operations further comprise:
    simulating transmembrane potentials at a plurality of locations in the patient-specific anatomical heart model using the personalized computational cardiac electrophysiology model.

22. The non-transitory computer readable medium of claim 21, wherein the operations further comprise:
    calculating body surface potentials at a plurality of locations on the patient-specific anatomical torso model based on the simulated transmembrane potentials; and
    generating a simulated ECG signal based on the body surface potentials.

23. The non-transitory computer readable medium of claim 19, wherein the operations further comprise:
    simulating one or more cardiac electrophysiological interventions using the personalized computational cardiac electrophysiology model.

24. The non-transitory computer readable medium of claim 19, wherein personalizing a computational cardiac electrophysiology model using a trained deep neural network (DNN) comprises:
    calculating spatially varying patient-specific conduction velocity values based on the ECG trace of the patient using the trained DNN.

25. The non-transitory computer readable medium of claim 19, wherein the trained DNN is trained using synthetic training samples having known ground truth ECG traces and known ground truth values for the parameter of the computational cardiac electrophysiology model, and each of the synthetic training samples is generated by randomly sampling values for the parameter of the computational cardiac electrophysiology model for a plurality of regions of a cardiac geometry in predetermined ranges for the regions, simulating transmembrane potentials in the cardiac geometry using the computational cardiac electrophysiology with the randomly sampled values for the parameter, propagating the simulated transmembrane potentials to body surface potentials on a torso geometry, and generating an ECG trace based on the body surface potentials.

* * * * *